(12) United States Patent
Eker et al.

(10) Patent No.: US 7,308,363 B2
(45) Date of Patent: Dec. 11, 2007

(54) MODELING AND EVALUATION METABOLIC REACTION PATHWAYS AND CULTURING CELLS

(75) Inventors: Steven Mark Eker, Menlo Park, CA (US); Patrick Denis Lincoln, Woodside, CA (US); Peter D. Karp, San Mateo, CA (US); Pedro Romero, Indianapolis, IN (US)

(73) Assignee: SRI International, Menlo Park, CA (US)

( * ) Notice: Subject to any disclaimer, the term of this patent is extended or adjusted under 35 U.S.C. 154(b) by 27 days.

(21) Appl. No.: 10/055,775

(22) Filed: Jan. 23, 2002

(65) Prior Publication Data

US 2003/0154003 A1    Aug. 14, 2003

(51) Int. Cl.
*G01N 33/48* (2006.01)
*G06F 7/60* (2006.01)
*G06G 7/48* (2006.01)

(52) U.S. Cl. .............................. 702/19; 702/20; 703/2; 703/11

(58) Field of Classification Search .................. 702/19, 702/27
See application file for complete search history.

(56) References Cited

U.S. PATENT DOCUMENTS

| | | | |
|---|---|---|---|
| 5,113,342 A | 5/1992 | Zamora | |
| 5,621,671 A | 4/1997 | Bodnar | |
| 5,805,461 A | 9/1998 | Fant et al. | |
| 5,914,891 A | 6/1999 | McAdams et al. | |
| 5,930,154 A | 7/1999 | Thalhammer-Reyero | |
| 5,980,096 A | 11/1999 | Thalhammer-Reyero | |
| 6,132,969 A | 10/2000 | Stoughton et al. | |
| 6,438,496 B1 | 8/2002 | Yoshida et al. | ............... 702/19 |
| 2002/0068269 A1 | 6/2002 | Allen et al. | |
| 2003/0033126 A1 | 2/2003 | Lincoln et al. | |

FOREIGN PATENT DOCUMENTS

WO    WO 99/66067    12/1999

OTHER PUBLICATIONS

Akutsu et al., Bioinformatics, vol. 16, pp. 727-734, 2000.*
Goto et al., Bioinformatics, vol. 14, pp. 591-599, 1998.*
Darnell et al., Molecular Cell Biology, 1987, pp. 53-63, 106-124, and 192-200.*
Akutsu et al., "Identification of Genetic Networks from a Small Number of Gene Expression Patterns Under the Boolean Network Model", *Bioinformatics* 17-28, 1999.
Akutsu et al., "Inferring qualitative relations in genetic networks and metabolic pathways", *Bioinformatics* 16(8):727-734 (2000).
Becskel et al., "Engineering stability in gene networks by autoregulation", *Nature* 405:590-593 (2000).
D'haeseleer et al., "Genetic network inference: from co-expression clustering to reverse engineering", *Bioinformatics* 16(8):707-726 (2000).
Endy and Brent, "Modelling cellular behaviour", *Nature* 409:391-395 (2001).
Gibbs, W.W., "Cybernetic Cells", *Scientific American* 53-57 (Aug. 2001).
Glass and Kauffman, "The Logical Analysis of Continuous, Non-linear Biochemical Control Networks", *J. Theor. Biol.* 39:103-129 (1973).
Karp, P.D., "An ontology for biological function based on molecular interactions", *Bioinformatics* 16:269-285 (2000).
Kauffman, S.A., "Metabolic Stability and Epigenesis in Randomly Constructed Genetic Nets", *J. Theoret. Biol.* 22:437-467 (1969).
Kohn, K.W., "Molecular Interaction Map of the Mammalian Cell Cycle Control and DNA Repair Systems", *Molecular Biology of the Cell* 10:2703-2734 (1999).
Liang et al., "Reveal, A General Reverse Engineering Algorithm for Inference of Genetic Network Architectures", *Proc. Pacific Symp. On Biocomputing* 3:18-29, 1998.
McAdams and Arkin, "Simulation of Prokaryotic Genetic Circuits", *Annu. Rev. Biophys. Struct.* 27:199-224 (1998).
Akutsu et al., "Identification of Genetic Networks from a Small Number of Gene Expression Patterns Under the Boolean Network Model", *Bioinformatics* 17-28 (1999).
Liang et al., "Reveal, A General Reverse Engineering Algorithm for Inference of Genetic Network Architectures", *Proc. Pacific Symp. On Biocomputing* 3:18-29 (1998).
McAdams and Shapiro, "Circuit Simulation of Genetic Networks", *Science* 269:650-656 (1995).
Mikulecky, D.C., "Modeling Intestinal Absorption and Other Nutrition-Related Processes Using PSPICE and STELLA", *Journal of Pediatric Gastroenterology and Nutrition* 11:7-20 (1990).
Novick and Weiner, "Enzyme Induction as an All-or-None Phenomenon*", *Proc. Nat. Acad. USA* 43:553-566 (1957).
Ogata et al., "Computation with the KEGG pathway database", *BioSystems* 47:119-128 (1998).
Ouzounis and Karp, "Global Properties of the Metabolic Map of *Escherichia coli*", *Genomic Research* 10:568-576 (2000).
Owre et al., "PVS: A Prototype Verification System", [11]th *International Conference on Automated Deduction (CADE)* 748-752 (1992).

(Continued)

*Primary Examiner*—Shubo (Joe) Zhou
(74) *Attorney, Agent, or Firm*—Kin-Wah Tong, Esq.; Patterson & Sheridan, LLP

(57) ABSTRACT

Biological and chemical systems are represented as a symbolic model. Minimal sets of elements of the system are identified from the model, for example, by automatic inference. The model can be constructed from Boolean propositions that are mapped to a binary decision diagram. The model can also be probed using a branch and bound algorithm.

26 Claims, 5 Drawing Sheets

OTHER PUBLICATIONS

Rosen, R., "Recent Developments in the Theory of Control and Regulation of Cellular Processes", *International Review of Cytology* 23:25-88 (1968).

Shea and Ackers, "The $O_R$ Control System of Bacteriophage Lambda A Physical-Chemical Model for Gene Regulation", *J. Mol. Biol* 181:211-230 (1985).

Snoussi and Thomas, "Logical Identification of All Steady States: The Concept of Feedback Loop Characteristic States", *Bulletin of Mathematical Biology* 55:973-991 (1993).

Somogyi and Sniegoski, "Modeling the Complexity of Genetic Networks: Understanding Multigenic and Pleiotropic Regulation", *Complexity* 1:45-64 (1996).

Stahl, W. R., "Algorithmically Unsolvable Problems for a Cell Automaton", *J. Theoret. Biol.* 8:371-394 (1965).

Stahl, W. R., "Self-Reproducing Automata", *Perspectives in Biology and Medicine* :373-393 (1965).

Stahl and Goheen, "Molecular Algorithms", *J Theoret. Biol.* 5:266-287 (1963).

Sugita, M., "Functional Analysis of Chemical Systems in vivo using a Logical Circuit Equivalent. II. The Idea of a Molecular Automaton", *J. Theoret. Biol.* 4:179-192 (1963).

Szallasi and Liang, "Modeling the Normal and Neoplastic Cell Cycle with "Realistic Boolean Genetic Networks": Their Application for Understanding Carcinogenesis and Assessing Therapeutic Strategies", *Proc. Pacific Symp. On Biocomputing* 3:66 (1998).

Thomas, R., "Boolean Formalization of Genetic Control Circuits", *J. Theor. Biol.* 42:563-585 (1973).

Thomas, R., "Regulatory Networks Seen as Asynchronous Automata: A Logical Description", *J. Theor. Biol.* 153:1-23 (1991).

Thomas et al., "A Complex Control Circuit: Regulation of Immunity in Temperature Bacteriophages", *Eur. J. Biochem.* 71:211-227 (1976).

Thomas et al., "Dynamical Behaviour of Biological Regulatory Networks—I. Biological Role of Feedback Loops and Practical Use of the Concept of the Loop-Characteristic State", *Bulletin of Mathematical Biology* 57:247-276 (1995).

Weng et al., "Complexity in Biological Signaling Systems", *Science* 284:92-96 (1999).

Yuh et al., "Genomic Cis-Regulatory Logic: Experimental and Computational Analysis of a Sea Urchin Gene", *Science* 279:1896-1902 (1998).

\* cited by examiner

MODELING AND EVALUATION METABOLIC REACTION PATHWAYS AND CULTURING CELLS

TECHNICAL FIELD

This invention relates to modeling reaction pathways.

BACKGROUND

Biological systems, for example, are governed by a complex network of chemical reactions. These reactions include metabolic reactions that participate in the formation of compounds essential for the viability of cells and the destruction of waste and toxic compounds. Other reactions include chemical reactions that are involved in regulatory and signaling processes. For example, signals detected at the cell surface can initiate a cascade of chemical reactions that result in the transcription of certain genes. Biological systems are characterized by both the large number of distinct compounds and the reactions that inter-relate them.

Formal mathematical tools have been developed to model complex artificial networks, such as computer circuit design and architectures for fault-tolerant systems. Many of these tools use aspects of Boolean logic to provide robust representations of complex systems.

SUMMARY

The invention provides, in part, models and methods of evaluating networks of chemical reactions.

In one aspect, the invention features a method (e.g., a machine-based method) that includes: generating a symbolic model that represents a network comprising chemical reactions; and evaluating the symbolic model to identify a set of precursor compounds and/or chemical reactions that are sufficient to produce a set of target compounds or a set of precursor compounds and/or chemical reactions that are insufficient to produce the set of target compounds. A plurality of sets can be identified. The set or sets can be a minimal set. Further, the method can identify any arbitrary number of, up to and including all sets that are sufficient are identified.

Before evaluating the model, the number of elements in the model can be reduced, e.g., using one or more of the following: bootstrap elimination, impossible rule deletion, needed compound elimination, factoring by equivalences, simplifying LHS/RHS overlaps, LHS subsumption, useless compound elimination, and reaction combination.

The symbolic model can include a Boolean function that returns a predetermined value (e.g., true or false) if the set of target compounds is produced. Such a function can be expressed in if-then-else normal form. Each if-then-else expression of the set can be mapped to a diagram of nodes, wherein each node of the diagram maps to an expression of the set of if-then-else expressions, depends on a Boolean variable associated with the expression and is directionally connected to two lower nodes in accordance with relationships implied by the expression, wherein each of the two lower nodes is either a node that maps to another expression of the set or a terminal node. The diagram is typically a decision diagram such as a so-called binary decision diagram. Evaluating can include identifying a path from a node of the diagram that is not a lower node of any other node to one of the terminal nodes of the diagram. In some implementations, a least-cost path is identified.

In a related aspect, the invention features a method that includes: representing a network of chemical reactions as a symbolic model, the model comprising elements that include compounds and reactant-product relationships between compounds; determining a Boolean function from the symbolic model, wherein the Boolean function returns a predetermined value (e.g., true or false) if the network produces a set of target compounds; and evaluating the Boolean function to identify a set of precursor compounds and/or relationships that is sufficient to produce the set of target compounds and/or a set of precursor compounds and/or chemical reactions that are insufficient to produce the set of target compounds. In some implementations, more than one Boolean functions are determined from the model. Further more, more than one network can be analyzed, e.g., to generate one or more Boolean functions.

The number of elements of the model can be reduced, e.g., prior to the evaluating, as described. In some implementations, the model is transformed, e.g., prior to the evaluating, and the evaluating includes evaluating a Boolean function determined from the transformed model. The result of evaluating the transformed model can be transformed back to provide a result for the original model.

The evaluating can include finding one or more—e.g., any number up to and including all—implicants (e.g., prime implicants) and/or implicates (e.g., prime implicates) of the Boolean function. Exemplary methods for finding implicants and implicates include use of a binary decision diagram, a branch-and-bound algorithm, and a fixed point method.

The method can include, for example, receiving information about the network of chemical reactions and generating the stored symbolic model from the information.

In another aspect, the invention features a method that includes: representing a network of chemical reactions as a symbolic model, the model comprising elements that include compounds and reactant-product relationships between compounds; reducing the number of elements in the model; and evaluating the model to identify a set of precursor compounds and/or relationships that is sufficient to produce the set of target compounds and/or a set of precursor compounds and/or chemical reactions that are insufficient to produce the set of target compounds. The reducing can include, for example, reducing the number of compounds and/or relationships in the model. Methods for reducing the model include bootstrap elimination, impossible rule deletion, needed compound elimination, factoring by equivalences, simplifying LHS/RHS overlaps, LHS subsumption, useless compound elimination, and reaction combination. In some implementations, the reducing includes iteratively removing elements of the model, e.g., repeatedly applying a reducing process until no further reduction is obtained. One exemplary process includes transforming the model, identifying a solution for the transformed model, and transforming the solution to identify the set of precursor compounds and/or relationships that is sufficient to produce the set of target compounds.

In still another aspect, the invention features a method that includes: representing a network of chemical reactions as a symbolic model, the model comprising elements, at least some of the elements representing compounds, and at least some elements representing reactant-product relationships between compounds; and automatically deducing from the model a set of the elements that determine a production state of the network. The deduced set can include a reduced number of elements relative to number of elements in the model. For example, the deduced set can be a minimal set.

The method can infer any arbitrary number of, up to and including all sets of elements that determine a production state.

The deduced set can include compounds that are reactants, e.g., precursor compounds. For example, the deduced set can include only those transportable compounds that are required for a production state. The deduced set can also include reactant-product relationships. In some implementations, the deduced set includes only reactant-product relationship or only compounds.

The model can include a monotone Boolean function.

In one exemplary inquiry, the production state is such that one or a set of target compounds is produced. Target compounds can be desired products of an artificial reaction system or, in another example, compounds essential for viability of a living cell. In another exemplary inquiry, the production state is such that at least one target compound is not produced, e.g., such that each compound of a set of target compounds is not produced.

In some implementations, the model includes Boolean propositions, e.g., if-then-else expressions. The model can be mapped to a diagram that includes nodes. Each node depends on a Boolean variable associated with one of the if-then-else expression and is directionally connected to two lower nodes in accordance with relationships implied by the expression. Each of the two lower nodes is either a node that maps to another expression of the set or a terminal node associated with a constant, e.g., 1 or 0.

For example, the model can be mapped to a binary decision diagram.

The model can include a Boolean function that depends on variables, each variable indicating a presence of a precursor compound. The function returns a predetermined value (e.g., true or false) for every case in which a set of target compounds can be formed from the precursor compound.

The deducing can include transforming the model to a second model, e.g., by reducing the number of relationships or a reduced number of reactants relative to the model before transformation or by problem-type transformation. The second model, for example, can enable determining of a set of compounds that indicate a set of relationships that determine a production state of the network.

The reactants of the model can include, for example, bootstrap compounds, metabolites, enzymes, nucleic acids, or agents (e.g., toxic, therapeutic, potentially therapeutic, or pathogenic agents.) Nucleic acids can be RNA or DNA molecules, including catalytic nucleic acids, coding and regulatory nucleic acids, and their allelic variants. Other reactants can be regulatory or structural proteins, including components such as a chromatin protein or a cytoskeletal protein.

The reactant-product relationships can include, e.g., a relationship at least between a reactant that is a gene and a product that is a polypeptide encoded by the gene and a relationship at least between a reactant that is a polypeptide and a product that is a modified form of the polypeptide. The modified form can be, for example, a phosphorylated, proteolyzed, glycosylated, methylated, or ubiquitinated form. Signaling polypeptides may be among those modified.

The method can be used for a model in which at least some elements of the deduced set are associated with a cost and the deducing includes identifying a least-cost set of elements, e.g., from among the minimal sets.

The method can also include formulating a medium for growth of the living cell such that the medium includes, e.g., all of the transportable compounds of the deduced set, or each transportable compound of the deduced set less one of the compounds of the deduced set. A living cell can be cultivated in the medium.

The method can be used to identify conditions that related to a cell behavior, e.g., cell proliferation, cell motility, or apoptosis. The target compounds can include a modified protein or proteins that are required for the cell behavior.

In a further aspect, the invention features a method that includes: representing each of a first and a second networks of chemical reactions as a symbolic model, each model comprising a plurality of elements; and deriving from the model a minimal set of elements of the first network that is not a minimal set of elements of the second network with respect to whether the first and second networks satisfy a given condition. The given condition can include production or non-production of a complete set of products essential for the viability or other behavior of the first and/or second living cell.

The method can include deriving any arbitrary number up to and including all sets of elements of the first network that are not minimal sets of elements of the second network are derived and/or comparing a set of minimal sets of elements of the first network to a set of minimal elements of the second network. The deriving can include logically deducing.

For example, the first network of chemical reactions can represent chemical reactions in a first living cell, and the second network of chemical reactions can represent chemical reactions in a second living cell. The chemical reactions can be intracellular and/or extracellular. They can map reactants to products. At least some of the reactants can include transportable compounds, e.g., compounds transportable into the first and/or second living cell.

The plurality of elements can include transportable compounds, and the method can include deriving a minimal set of transportable compounds such that when any one or more transportable compounds of the minimal set are withheld, the first network does not produce a complete set of essential products for the viability of the first living cell, but the second network does produce a complete set of essential products for the viability of the second living cell. In a related inquiry, the derived minimal set can be such that when each transportable compound of the set is withheld, the first network does not produce a complete set of essential products for the viability of the first living cell, but the second network does produce a complete set of essential products for the viability of the second living cell.

The method can include culturing the first and/or second living cell under culture conditions in which one or more compounds of the minimal set of transportable compounds is withheld.

Still other related inquiries relate to deriving a minimal set of chemical reactions such that when any one or more (and in some cases all) chemical reactions of the minimal set is blocked, the first network does not produce a complete set of essential products for the viability of the first living cell, but the second network produces a complete set of essential products for the viability of the second living cell. The method can include cultivating the first and/or second living cell in the presence of an inhibitor, the inhibitor blocking a chemical reaction of the minimal set of chemical reactions or inhibitors that block each chemical reaction.

For example, the first living cell can be a pathogen cell and the second living cell a host cell. In another example, the first living cell is a mammalian cell, e.g., a diseased mammalian cell, e.g., having an aberrant proliferative and/or abnormal differentiative state. In some particular embodiments the first living cell is a cancer cell. Of course, the second living cell can be a mammalian cell, e.g., having a normal proliferative and/or normal differentiative state.

The deducing can include identifying at least first and second Boolean functions, the first Boolean function expressing relationships between elements in the first network, and the second Boolean function expressing relationships between elements in the second network. The method can also include representing a third network of chemical reactions as a symbolic model, and, for example, deriving from the model a minimal set of elements of the first network that is not a minimal set of elements of the second or third networks with respect to whether the first, second, and third networks satisfy a given condition.

In another aspect, the invention features a method of representing a chemical reaction network as a Boolean function. For a network that includes relationships between compounds, the relationships representing chemical reactions and the compounds including precursor compounds and target compounds, the method can infer a Boolean function that depends on variables where each variable indicates a presence of one of the precursor compounds, and the function returns a predetermined value (e.g., true or false) for every case in which the target compounds can be formed from the precursor compounds.

The method can include identifying an implicate and/or implicant of the Boolean function, e.g., prime forms thereof. Any arbitrary number, up to and including all prime implicants or prime implicants of the Boolean function can be identified.

The function can be transformed a binary decision diagram. The function can be inferred by recursively constructing a symbolic representation of the Boolean function from subexpressions corresponding to the relationships between reactants. The symbolic representation can include nodes, each node corresponding to a variable. In one example, the representation is a truth table (e.g., a compact truth table) for the function.

A related method includes defining a Boolean function that models a chemical reaction network, returns a predetermined value if each of a first group of network elements is in a defined state, and depends on variables hat each describe a state of an element from a second group of network elements; and comparing variables from first sets of variables to infer a second set of variables, each first set of variables being a minimal set that returns the predetermined value for the function, the second set of variables being a set that returns the predetermined value for the function and differs from each first set of variables. The method can include a branch and bound algorithm. For example, the method can include minimizing the second set of variables by iteratively testing each variable of the second set to determine if it is required for the function to return the predetermined value. A variable can be discarded from the second set after it is tested and before another variable of the second set is tested.

The comparison of variables from the first sets can include identifying a third set of variables, each variable of the third set being true if the variable is true in at least one of the first sets; and inferring the second set of variables by negating the third set of variables.

The invention also features a machine-based method that includes expressing relationships between compounds, the relationships representing chemical reactions and the compounds including precursor compounds and target compounds; and identifying any arbitrary number of, up to and including all, minimal sets of elements, each set being sufficient or required for production of the target compounds.

Each method described herein can also include generating an output that includes a result of the method, e.g., displaying the result to a user, storing the result, or transmitting a result to a user, a system, or a storage device. Model, functions (e.g., Boolean functions), results, parameters, and results (e.g., implicates and implicates) can also be stored, e.g., in digital form on a machine-accessible medium. Instructions for performing each method can also be stored on a machine-accessible medium. Also included are machine-based systems configured to execute each method. Each chemical network or model can include, for example, at least 5, 20, 100, 500, 1000, 2000, or 5000 chemical reactions.

Other advantages and features of the invention will become apparent from the following description and from the claims.

DETAILED DESCRIPTION

Figure 1:
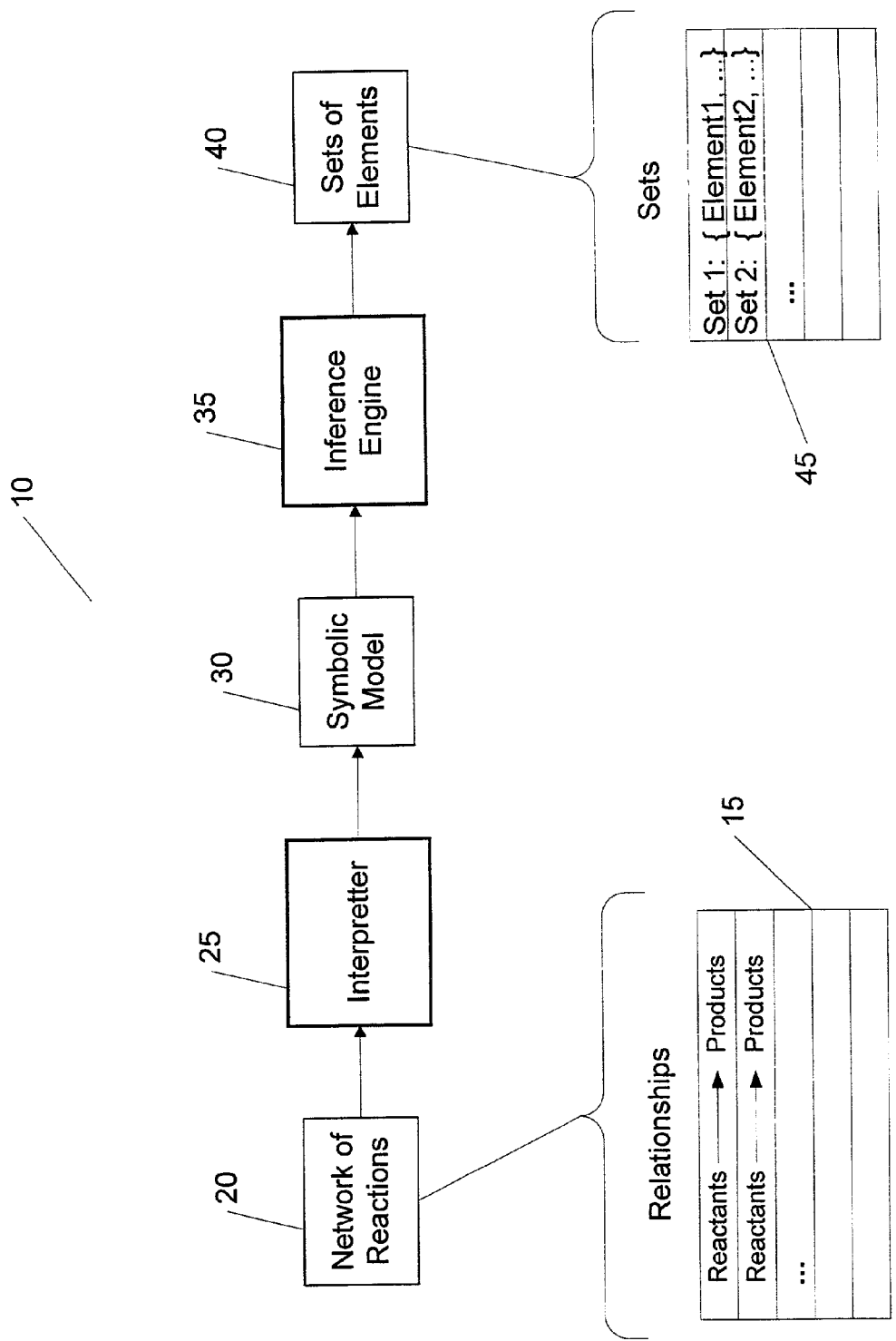
FIG. 1 is a flow chart of an exemplary method for generating and using a symbolic model.

Cells depend on their ability to produce certain compounds for viability. Cells generally obtain compounds from their environment and metabolize them to produce those compounds that are essential for their viability. Metabolic pathways involve components including enzymes, cofactors, substrates, and products. Some of these compounds are reaction intermediates. Chemical reactions describe the interrelationships of these pathway components. Given that the details of numerous metabolic pathways can be elucidated by experimental work, it is now possible to analyze this information using models to derive useful information about conditions that support or prevent viability.

Aspects of the Model

The model includes representations for at least four different aspects of the cellular system. Each aspect includes a different class of elements of the system.

The first aspect represents a set of compounds that are considered end-products required for survival of the cell. These are referred to as "essential compounds." Of course, this designation is flexible because it constitutes an arbitrary reference point for the model. For example, an amino acid that is an end-product of an amino acid biosynthetic pathway, while being required for survival, is also a precursor for protein synthesis. In another example, an intermediate in the pathway for the synthesis of the amino acid is clearly also required for survival, but in that example, the intermediate would not be designated as an "essential compound."

The second aspect represents a set of compounds that are considered available from the environment and that can be used to synthesize the essential compounds. These are referred to as "transportable compounds." This designation, too, is flexible and arbitrary in the sense that, for the purposes of modeling, a compound that is not generally available from the environment (such as a pharmacological agent) can be considered a transportable compound. In the context of reactions that occur within or immediately surrounding cells (e.g., in the periplasm or on the cell surface), transportable compounds can encompass compounds that can enter cells or the immediate environment of a cell (e.g., the periplasm or the cell surface. In the context of reactions that occur in an in vitro system, transportable compounds can encompass the compounds, contemplated by the model, which could be supplied to the system.

The third aspect represents a set of compounds that are assumed to always be present in the cell. These compounds include, for example, water and cofactors for enzymes such as nicotinamide adenine diphosphate (NAD). These compounds are referred to as "bootstrap compounds." Again, the designation is flexible and arbitrary. For example, water is required for survival and is available in the environment. However, for the purposes of a given model, it may be most effective to classify water as a bootstrap compound.

The fourth aspect represents the chemical reactions that can occur in the cells. The chemical reactions are expressed as statements that indicate the formation of products dependent on the reactants. The essential compounds are the products of some of the reactions. Likewise, the transportable compounds are the reactants of some of the reactions. In addition, the products and reactants can be intermediate compounds that are neither essential compounds nor transportable compounds. Some of these reactions can be used to synthesize the essential compounds from the transportable compounds. The experimental characterization of the metabolic pathways of some cells provides information about the reactions that can occur in cells. Some of the resulting information has been collated in diagrams (e.g., the Boehringer Biochemical Pathways Wall Chart from Boehringer Mannheim GmbH—Biochemica, Roche Molecular Biochemicals) and databases (e.g., EcoCyc; Karp et al. (2000) Nucl. Acids Res. 28:56-59).

The essential compounds, the transportable compounds, the bootstrap compounds, and the chemical reactions define the state of the system or the "specification". As these four aspects of the system are inter-related, information about three of them can be used to infer information about the fourth.

Symbolic Expression

Information about each of the aspects and about the specification is expressed symbolically. The presence of each compound is expressed as a logical proposition. When evaluated, the logical proposition can be "TRUE" or "1", representing the presence of the compound, or "FALSE" or "0", representing the absence of the compound. The presence of a set of compounds is represented as a conjunction of logical propositions.

This logical representation is now used to represent chemical reactions, which are typically described in chemical texts using the notation of expression (1):

(1)

According to the notation of expression (1), the reactants $p_1, \ldots, p_n$ react with each other to form products $q_1, \ldots, q_m$. In other words, if compounds on the left-hand side of the arrow are present, compounds on the right-hand side are produced. In the implementation described here, this chemical reaction is represented now as a logical proposition that is the conjunction of propositions (2):

(2)

In this expression, each of $P_1, \ldots, p_n$ and $q_1, \ldots, q_n$ is a proposition that represents the presence or absence of a compound, e.g., a reactant for $p_i$ and a product for $q_i$. The expression $p_1 \wedge \ldots \wedge p_n$ is TRUE if all the reactants are present. This expression implies that all the products are present. Hence, the expression $q_1 \wedge \ldots \wedge q_m$ is TRUE. Each individual proposition, e.g., $q_1$, must be TRUE for the expression $q_1 \wedge \ldots \wedge q_m$ to be TRUE. Thus, the logical propositions for each of the individual products indicate that they are present.

Specification

A set of propositions is defined for each aspect of the model. B is a set of propositions corresponding to the set of bootstrap compounds; T is a set of propositions corresponding to the set of transportable compounds; R is a set of formulae corresponding to the set of reactions; and E is a set of propositions corresponding to the set of essential compounds.

Formally, the specification Z is expressed by the following 4-tuple:

$$Z = <B, T, R, E> \qquad (3)$$

where B, T, R, and E are the sets of propositions described above.

Inquiries of the System

A variety of inquiries can be made of the specification that reveal the properties of the cellular system modeled by the specification. The following four examples of inquiries are numbered for reference:

1: What is a set of transportable compounds that results in the synthesis of the complete set of essential compounds?

2: What is a set of reactions that results in the synthesis of the complete set of essential compounds?

3: What is a set of transportable compounds that, if withheld, prevents the synthesis of the complete set of essential compounds?

4: What is a set of reactions that, if blocked, prevents the synthesis of the complete set of essential compounds?

Other kinds of inquiries are also useful.

The inter-relationships of these different inquiries are diagrammed in Table 1. Inquiries #1 and #3 both relate to the transportable compounds, whereas inquiries #2 and #4 relate to the chemical reactions. Inquiries A and B on a given row are concepts that are dual to each other.

TABLE 1

| Relevant Set | Inquiry A | Inquiry B |
|---|---|---|
| T | Set required for E (#1) | Withheld Set to block E (#3) |
| R | Set required for E (#2) | Withheld Set to block E (#4) |

For each set that is a solution to the above inquiry, a minimal set can be identified that is also a solution. It can be useful to (a) identify all such minimal sets; (b) find some large number of minimal sets (in case there are too many list all); (c) find one or all of the smallest such minimal sets; and/or (d) count the number of minimal nutrient sets.

Other operations with respect to minimal sets are also useful. For example, maximum superfluous sets can be identified by subtracting the minimal sets from a complete set. Hence, a maximum superfluous set of nutrients is the set of nutrients that a cell can grown without. This set is the set of all available nutrients except for those members that are in the minimal nutrient set.

Minimal Nutrients (#1). The solution to the first inquiry (#1: What is a set of transportable compounds that results in the synthesis of the complete set of essential compounds?) identifies a set of transportable compounds that are required for the viability of the cell being modeled.

A set N can be defined which is a subset of the possible transportable compounds T such that the complete set of essential compounds E is produced. N can be define in the context of the specification Z=<B, T, R, E>:

A subset $N \subseteq T$ is a nutrient set iff B, N, R⊢ E. The latter expression is the provability relationship expressed in propositional calculus. It can be translated: as given the set of bootstrap compounds B, a set of nutrients N that is a subset of the set of possible transportable compounds T, and the set of reactions R, each compound of the complete set of essential compounds E is produced.

A nutrient set N is a minimal nutrient set if no proper subset of N is a nutrient set. The term "minimal" indicates that the set cannot be further reduced.

A minimal nutrient set N is a smallest minimal nutrient set iff no other minimal nutrient set has fewer elements.

Biological systems can include many redundant pathways for the synthesis of a particular compound. For example, if an essential compound, E1, can be synthesized from either of two transportable compounds P1 or P2, then it is apparent that one solution to the inquiry is a set that includes P1, i.e., {P1}, and another set that includes P2, i.e.,{P2}. Supposing that P1 and P2 are not required for any other essential compound, a set that includes P1 and P2 {P1, P2} is also a solution, but this is not a minimal set.

Identifying a minimal nutrient set provides an answer to Inquiry #1. A biological example of a minimal nutrient set is the set {glucose, $KH_2PO_4$, $(NH_4)_2SO_4$, $MgSO_4.7H_2O$, $FeSO_{40}.7H_2O$, KOH and water}. This set is a minimal nutrient set for some strains of *E. coli*. It can be of experimental, diagnostic, and therapeutic interest to determine the minimal nutrient set for a cell, for example, if the cell is a cell of a pathogen or a diseased cell, e.g., a cancer cell. Further, identification of the set of all minimum nutrient sets may provide a holistic view of the cell's requirements and susceptibilities. The set of all minimal nutrient sets is also termed the complete set of all minimal nutrient sets.

Minimal Starvation Set (#3). A related inquiry is the identification of compounds, whose absence results in death of a cell. Such compounds are considered starvation compounds. Withholding a minimal set of starvation compounds would result in death of the cell. Withholding one fewer than the minimal set of starvation compounds would allow the cell to live. The minimal set of starvation compounds, S, is a logical dual of the minimal set of nutrients N.

Given a specification Z=<B, T, R, E>:

A subset $S \subseteq T$ is a starvation set if it is not true that B, (T\S), R⊢ E. This provability relationship implies that given the set of bootstrap compounds B, the set of compounds that includes each of the possible transportable compounds T except those in subset S, and the set of reactions R, at least one of the essential compounds from the set E is NOT produced.

A starvation set N is a minimal starvation set if no proper subset of N is a starvation set.

A minimal starvation set N is a smallest minimal starvation set iff no other minimal starvation set has fewer elements.

A starvation set provides a solution to Inquiry #3:

Minimal Reaction Set (#2). Similarly, a set is defined that is the solution to Inquiry #2 (What is a set of reactions that results in the synthesis of the complete set of essential compounds?). This set, which is also referred to as a proof set P, is a subset of R, the set of reactions.

Given a specification Z=<B, T, R, E>:

A subset $P \subseteq R$ is a proof set iff B, T, P⊢ E. This provability relationship implies that given the set of bootstrap compounds B, a set of nutrient N that are a subset of the set of possible transportable compounds T, and the set of reactions P (which is a subset of R), each compound of the complete set of essential compounds E is produced.

A proof set P is a minimal proof set if no proper subset of P is a proof set.

A minimal proof set P is a smallest minimal proof set iff no other minimal proof set has fewer elements.

Intuitively, a proof set is a set of reactions that enables a cell to survive on the set of transportable compounds T. A proof set is also a set of reactions that are sufficient to prove that a cell can survive on the set of transportable compounds T.

Minimal Knock-Out Set (#4). A set is defined that is the solution to Inquiry #4 (What is a set of reactions that, if blocked, prevents the synthesis of the complete set of essential compounds?). This set is referred to as a knockout set or K.

Given a specification Z=<B, T, R, E>:

A subset $K \subseteq R$ is a knockout set iff it is not true that B, T, (R\K)⊢ E. This provability relationship implies that given the compounds of set B and T, and the set of reactions R, except those in K, at least one of the essential compounds from set E is NOT produced.

A knockout set K is a minimal knockout set if no proper subset of K is a knockout set.

A minimal knockout set K is a smallest minimal knockout set iff no other minimal knockout set has fewer elements.

Intuitively, a knockout set is a set of reactions that if disabled will kill the cell. The identification of a knockout set can guide a drug discovery effort. Compounds that block the reactions of a knockout set can be administered in combination in order to kill a cell.

All four of the exemplary inquiries described above can be addressed using by identifying a Boolean function that describes the specification. This function is termed the "characteristic function."

Characteristic Function

One method of identifying a minimal set is to define a Boolean function,$f_Z$, termed the characteristic function. $f_Z$ depends on a Boolean vector, $v_N$, that reflects the availability of compounds from T, the set of transportable compounds.

At this level of the model, the function is monotonic and idempotent. Monotonicity indicates that compounds are not consumed. Once a compound is determined to be present, it remains so. Thus, provisions are not required to determine if another reaction would remove the compound. For example, negative feedback loops are not considered at this level. Idempotency indicates that the exact concentration of compounds are not considered. For example, in some implementations, a threshold concentration is set for each compound. Once the threshold is attained, the compound is considered to be present. The threshold can be a limit of detectability or a concentration at which the compound is effective biologically or chemically.

The characteristic function $f_Z$ is defined as follows:

Let the transportable compounds, T, be linearly ordered, say $t_1, \ldots, t_k$. The ordering allows the Boolean vector $v_N$ to be defined.

For each subset $N \subseteq T$, let $v_N$ denote the Boolean vector where the ith component is 1 iff $t_i \in N$.

A specification $Z=<B, T, R, E>$ defines a monotone Boolean function $f_Z: B^k \rightarrow B$ termed the characteristic function of Z by $$f_Z(v_N)=1 \text{ iff } B, N, R \vdash E \qquad (4)$$

In other words, the function $f_Z$ returns 1 if the available transportable compounds (N) imply that the complete set of essential compounds E is synthesized. N is the subset of transportable compounds T that are available. $f_Z$ returns 0 in every other instance.

The characteristic function is a useful tool for identifying solutions to the minimal set inquiries. Solutions for a monotone Boolean function of a Boolean vector can be described as implicants and implicates. An implicant I is a set of variables that if set to 1 cause f to return 1, independent of the state of the other variables. An implicant I of f is a prime implicant of f if no proper subset of I is an implicant of f.

An implicate J of f is a set of variables, that if set to 0 cause f to return 0 independent of the state of the other variables. An implicate J of f is a prime implicate of f if no proper subset of J is an implicate of f. The implicant and implicate are dual notions.

Solutions to the set inquiries described above (Inquiries #1, #2, #3, and #4) can be directly determined from the implicants and implicates of the characteristic function. For example, the minimal nutrient sets, i.e., the solutions to Inquiry #1, correspond to the prime implicants of $f_Z$. The minimal starvation sets, i.e., the solutions to Inquiry #3, correspond to the prime implicates of $f_Z$. Just as the implicant and the implicate are dual notions, as mentioned above, the inquiries themselves are duals of each other. Referring back to Table 1, in each row, the inquiry in the column "Inquiry A" is a dual of the inquiry in the adjacent column, "Inquiry B."

Solutions to the Inquiries

For each inquiry related to the system, at least one set that is a solution can be derived from the characteristic function. Referring to FIG. 1, a process 10 is provided for obtaining solutions that are sets of elements 40 for a reaction network 20. A reaction network 20 includes a number of relationships 15 that indicate reactions between reactants to form products. The relationships are processed by an interpreter 25 which formulates a symbolic model 30 for the reaction network 20. This model 30 can include, for example, the characteristic function. An inference engine 35 then analyzes the model 30, for example, to automatically infer a solution 40 to inquiries about the model 30. The inference engine 35 outputs the solution 40. The solution can include one or more sets of elements. As described, a class of particularly useful solutions are sets that are minimal sets. Further, in some implementations, the inference engine can identify any arbitrary number, up to and including all minimal sets that are solutions to a given inquiry.

Identifying all possible minimal sets, however, demands a quantifiable degree of computation (see, e.g., Gurvich and Khachiyan (1999) *Discrete Applied Mathematics* 96/97:363-373). For example, determining the complete set of possible solutions (e.g., the complete set of prime implicants or prime implicates) for a Boolean function is generally co-NP-complete. Gurvich and Khachiyan, supra, demonstrate that for a monotone function Boolean function f defined by a $\wedge, \vee$ formula of depth 3 and a set C of prime implicants (implicates), the problem of deciding if C is the complete set of prime implicants (implicates) is co-NP-complete.

Likewise, for a monotone function Boolean function f that can be evaluated at any point there is a quasi-polynomial time algorithm for finding a next prime implicant or implicate. Hence, for complex characteristic functions, the identification of the set of all prime implicants or implicates requires significant computation. Strategies to reduce the complexity of characteristic functions prior to the search for these sets are, therefore, particularly useful.

Figure 2:
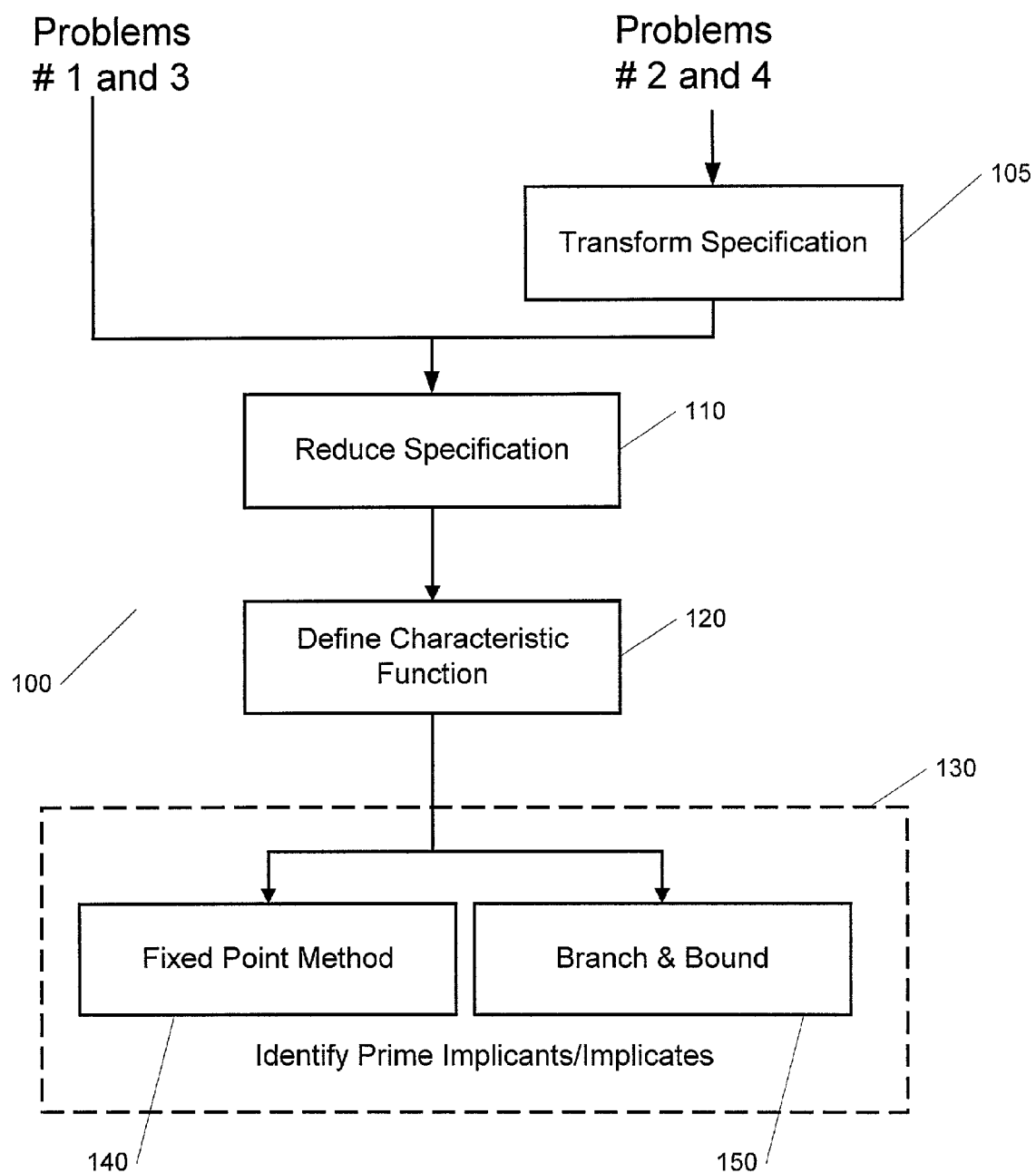
FIG. 2 is a flow chart of an exemplary method for identifying solutions for inquiries using a symbolic model.

Referring to FIG. 2, the process 100 is an exemplary flow for solving the inquiries labeled #1, #2, #3, and #4 above. For inquiries #2 and #4, which relate to the set of reactions, the specification for these inquiries is transformed 105 into a specification that is equivalent to the specification for inquiries #1 and #3. A variety of specification reduction strategies 110 are applied to reduce the problems to a smaller size. After specification reduction 110, the characteristic function for the reduced function is defined 120. One or more prime implicants or implicates are identified 130 for the characteristic function. The literal solutions to the inquiries are directly determinable from the prime implicants or implicates.

Specification Transformation

With respect to the minimal set Inquiries #2 and #4, which are related to the reactions, the specification Z is transformed 100 to a corresponding associated specification Z' as follows.

Given a specification $Z=<B, T, R, E>$, each reaction $(U_1 \rightarrow V_1) \in R$ is labeled with a fresh proposition $I_1$. Let L be the set of such labels. An associated specification $Z'=<B', T', R', E'>$ is defined as follows:

$B'=B \cup T$ $T'=L$

With respect to R', for each reaction in R include a corresponding reaction in R' as follows: $(U_i \rightarrow V_i) \in R$, include $(l_i \wedge U_i \rightarrow V_i) \in R'$.

$E'=E$.

Solving the minimal nutrient set inquiry (#1) for Z' solves the minimal proof set inquiry (#2) for Z and solving the minimal starvation set inquiry (#3) for Z' solves the minimal knockout set inquiry (#4) for Z. The transformation thus streamlines the processing of these related inquiries.

Specification Reduction

Figure 3:
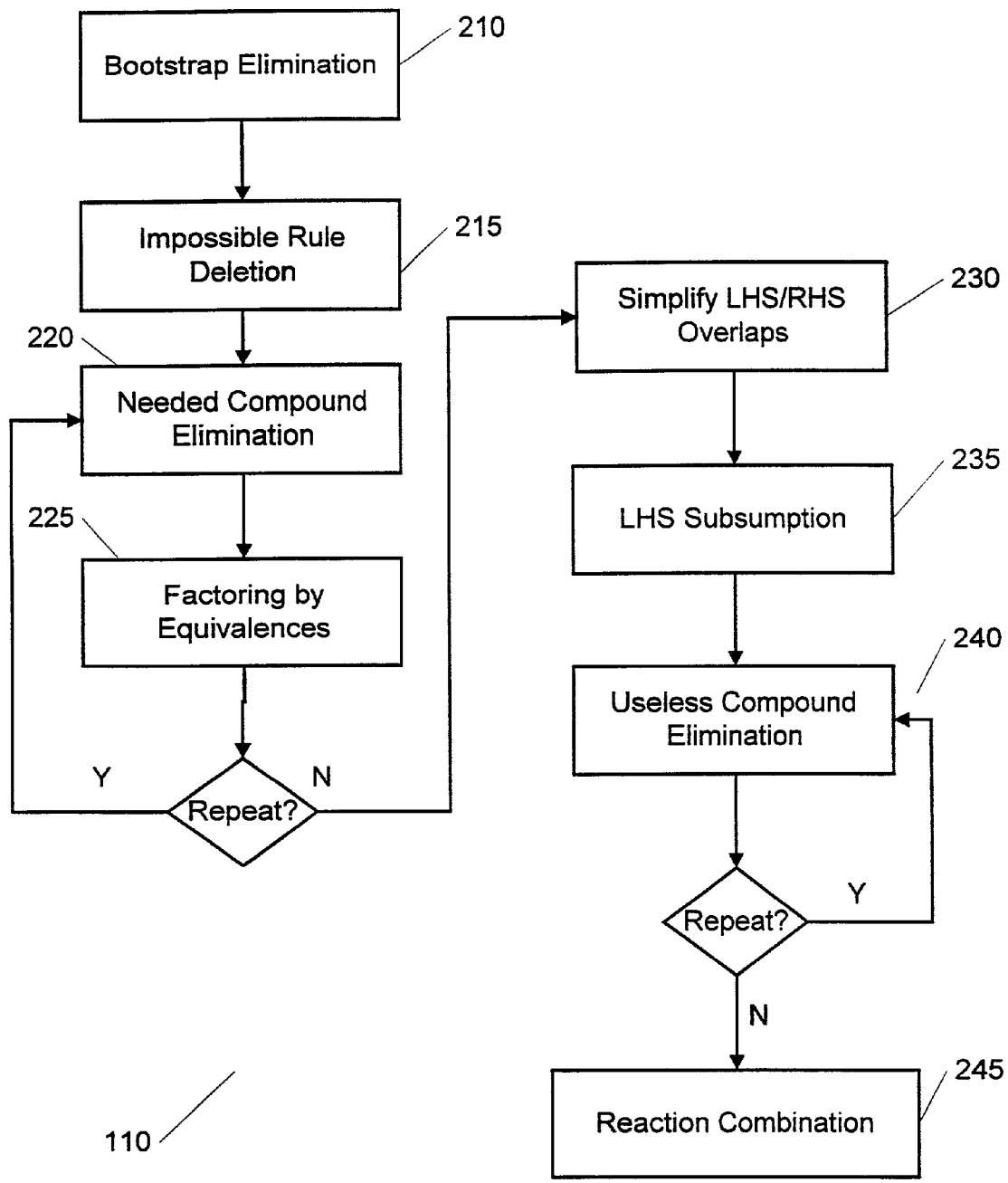
FIG. 3 is a flow chart of an exemplary method for reducing the complexity of a specification.

Referring to FIG. 3, a specification $Z=<B, T, R, E>$ can be reduced in complexity by a variety of reduction strategies 110. Some of these strategies take advantage of structural regularities in biological systems that can be factored out.

In one exemplary implementation, these strategies are applied as follows: bootstrap elimination 210, impossible rule deletion 215, one or more iterations of needed compound elimination 220 and factoring by equivalences 225, simplifying LHS/RHS overlaps 230, LHS subsumption 235, one or more iterations of useless compound elimination 240, and reaction combination 245. Details of each of these processes are below. The iterations can proceed until no additional reduction is obtained.

Bootstrap Elimination. This process simplifies the specification $Z=<B, T, R, E>$ to $Z''=<T, R, E>$ by removing the set of propositions for the bootstrap compounds. Realizing that the bootstrap compounds are always present, they need not be considered in the solution. For example, a reaction that uses water as a reactant for a substrate A might be first written: $A+H_2O \rightarrow B$. Considering that water is always present, and, thus, a bootstrap compound, the reaction can be rewritten as $A \rightarrow B$ without altering the solutions to the inquiries posed above.

Formally, for a specification Z=<B, T, R, E>, define $$\text{product}_R(X) = \{c | X, R \vdash c\} \quad (5)$$

That is for X, a set of compounds, the function $\text{product}_R$(X) returns the set of compounds that includes all compounds that are synthesized given only the compounds in X and the reactions R.

A bootstrap free specification Z'=<T', R', E'> is formed as follows:

T'=T\$\text{product}_R$(B), i.e., discard from transportable compounds T the compounds that are merely the products of the bootstrap compounds alone.

R'={(((U\$\text{product}_R$(B))→(V\$\text{product}_R$(B)))⊊(U→V)∈R and V\$\text{product}_R$(B) ≠∅}, i.e., restate the left and right side of each reaction by removing any compounds that are the products of the bootstrap compounds alone.

E'=E\$\text{product}_R$(B), prune from the set of essential compounds E any Compounds that are the products of the bootstrap compounds alone.

The minimal nutrient sets and minimal starvation sets of Z are identical to those of Z'.

Impossible Reaction Deletion. This strategy prunes the specification of reactions that can never occur. For example, if D is neither a transportable compound, nor the product of any other reaction, D is termed an impossible compound as there is no circumstance in which D could be present. Accordingly, a reaction that transforms D→F is termed an impossible reaction.

Generally stated, for a specification Z=(T,R,E), a compound c is impossible if given the transportable compounds T, and reactions R, the compound c is not produced. A reaction is impossible if it contains an impossible compound as a reactant.

To delete the impossible reactions, the set R' is created by removing all impossible reactions from R. The reduced specification Z' is defined by Z'=<T, R', E'>. Again, the solutions to inquiries with respect to Z or Z' are identical.

Needed Compound Elimination. This strategy prunes the specification of what might be considered "trivial" solutions to the inquiry as to which transportable compounds that are required to make the essential compounds. "Needed compounds" are compounds that, independent of the other transportable compounds that are available, are required for synthesizing the complete set of essential compounds.

A needed compound $c_{nd}$ can be formally defined for a specification Z=<T, R, E> as follows: A compound c ∈ T is needed iff if T\{c}, R⊬E. Needed compounds can be identified by simple forward analysis. For example, to determine if a compound c is needed, the reactions R are run using an initial set of T\{c} compounds until no new compounds are produced. If the final set does not contain all the essential compounds, then c is essential.

Let C be the set of needed compounds. We form a reduced specification Z'=<T', R', E'> as follows:

T'=T\$\text{product}_R$(C), i.e., T' is the set of transportable compounds pruned of all compounds that are produced by the needed compounds alone, including the needed compounds themselves. See equation (5) for the definition of $\text{product}_R$(C).

R'={(U\$\text{product}_R$(C)→V\$\text{product}_R$(C)) |(U→V)∈R and V\$\text{product}_R$(C)≠∅}, i.e., for each reaction in the set R, prune the left and right side of the set of compounds that are produced by the needed compounds alone and the needed compounds themselves, and remove reactions whose products depend only on the needed compounds that are produced by the needed compounds alone and the needed compounds themselves.

E'=E\$\text{product}_R$(C), i.e., E' is the set of essential compounds pruned of those essential compounds that are the products of needed compounds alone.

The minimal nutrient sets of Z are the minimal nutrient sets of Z' unioned with C. The minimal starvation sets of Z are those of Z' together with {c} for each c∈C. In other words, each set {c}, which contains only a single compound—one of the needed compounds—is a minimal starvation set, since withholding even that single needed compound is sufficient to prevent the complete set of essential compounds from being synthesized.

Factoring by Equivalences. This process identifies compounds, other than transportable compounds, that function equivalently in the specification.

For a specification Z=<T, R, E>, such compounds are identified by the equivalence relation ($\equiv_R$), as follows:

$$c \equiv_R d \text{ iff } \text{product}_R(\{c\}) = \text{product}_R(\{d\}) \quad (6)$$

The compounds are grouped into equivalence classes according to the relation (6). Then, for each equivalence class $[C]_{\equiv_R}$ that does not include a transportable compound, a representative member is selected such that $c^+ \in T$ if $[C]_{\equiv_R} \cap T \neq \emptyset$.

Z' is constructed from Z by replacing every compound c in the equivalence class with the selected representative $c^+$ of the equivalence class.

The system Z' may have fewer minimal nutrient sets than Z, for example. The missing minimal nutrient sets can be recovered by expansion. For each minimal nutrient set N' of Z', each c∈N' can be replaced by any $c' \in [c]_{\equiv_R} T$ forming a minimal nutrient set N of Z. The strategy also extends to the other minimal set solutions.

Simplifying LHS/RHS Overlaps. Reaction expressions are simplified by replacing products of reactions that are also reactants for the same reaction. The reactants are on the "left-hand side" (LHS) of the reaction expression and the products are on the "right-hand side" (RHS). Thus, the reaction C1+C2→C3+C2 can be simplified as C1+C2→C3. Reactions that appear in a structure that requires this simplification can arise from other reductions steps.

For a specification Z=<T, R, E>, a reduced specification Z'=<T, R', E> is constructed such that:

$$R' = \{(U \to V \setminus U) | (U \to V) \in R \text{ and } V \setminus U \neq \emptyset\} \quad (7)$$

The nutrient sets and starvation sets of Z are identical to those of Z'.

LHS Subsumption. Duplicate reactions are eliminated. For reactions U→V and U'→V', where U' ⊂ U, i.e., where at least some of reactants of the second reaction are the only reactants of the first reaction, the first reaction U→V can be simplified by removing products from the first reaction that are also products of the second reaction—that is replacing the first reaction with U→V\V'. If the products of both reactions are the same (i.e., V\V'=∅), the first reaction can be removed altogether. The nutrient sets and starvation sets are unaffected by this transformation.

Useless Compound Elimination. A "useless" compound is one that is neither an essential compound nor a reactant for another reaction. Useless compounds can be pruned from expressions in the set of reactions in order to reduce the size of the specification. Useless compounds are removed from the RHS (i.e., removed as products) from all the reaction statements. If only useless compounds are on the RHS, the reaction statement can be removed altogether.

Formally, for a specification Z=<T, R, E>, a compound c is "useless" iff c∉E and c does not occur in the LHS of a reaction. Let C be the set of useless compounds. A reduced specification Z'=<T, R', E'> is constructed where $$R' = \{(U \rightarrow V \setminus C) | (U \rightarrow V) \in R \text{ and } V \setminus C \neq \emptyset\} \quad (8)$$

The nutrient sets and starvation sets of Z are identical to those of Z'.

Reaction Combination. For reaction expression that have the same reactants, i.e., the same LHS, the expression can combined by using the common LHS and concatenating the RHS. Thus, the two reactions C1+C2→C3 and C1+C2→C4 can be combined as C1+C2→C3+C4.

For a specification Z=<T, R, E>, we define the function $rxn_R(U)$ which returns all reactions with the same reactants, is defined as follows:

$$rxn_R(U) = \{(U \rightarrow V) | (U \rightarrow V) \in R\}. \quad (9)$$

The reduced specification Z'=<T, R', E'> is specified by:

$$R' = \{(U \rightarrow V_1 \cup \ldots \cup V_k) | rxn_R(U) = \{(U \rightarrow V_1), \ldots, (U \rightarrow V_k)\}\} \quad (10)$$

Thus the set of expressions with the same reactants (or LHS) are replaced with one expression for the reactants. The new expression lists as products all the products of each set of reactants. Again, the nutrient sets and starvation sets of Z are identical to those of Z'.

Solving the Minimal Nutrient Problem

Referring again to FIG. 2, after reducing the complexity of the specification, two approaches can be used to identify solutions to the inquiries (e.g., #1, #2, #3, or #4).

One approach 140 is a so-called "fixed point method" which extracts prime implicants from a symbolic representation of the characteristic function $f_Z$ for the specification. In one implementation, the approach 140 uses binary decision diagrams as the symbolic representation.

A second approach 150 is to evaluate the characteristic function $f_Z$ as a "black box" monotone Boolean function. The function is searched for prime implicants, e.g., using the Gurvich-Khachiyan algorithm or a branch and bound algorithm.

Binary Decision Diagrams

Binary Decisions Diagrams (BDDs) are a representation of a Boolean function or, equivalently, propositional formulae. They are a form of a tree diagram in which equal subexpressions are identified and represented once. As a result, they compress the information that is provided by a truth table for the same function. For functions that have some regularity, the extent of compaction can be significant.

Typically, a BDD represents a Boolean expression as translated into an IF-THEN-ELSE normal form (INF). INF is a Boolean expression that is constructed from IF-THEN-ELSE subexpressions that operate exclusively on Boolean variables and the constants 0 and 1. It has been proven that any Boolean expression can be represented in INF. An INF is mapped to a BDD by representing each Boolean variable as a node.

Figure 4:
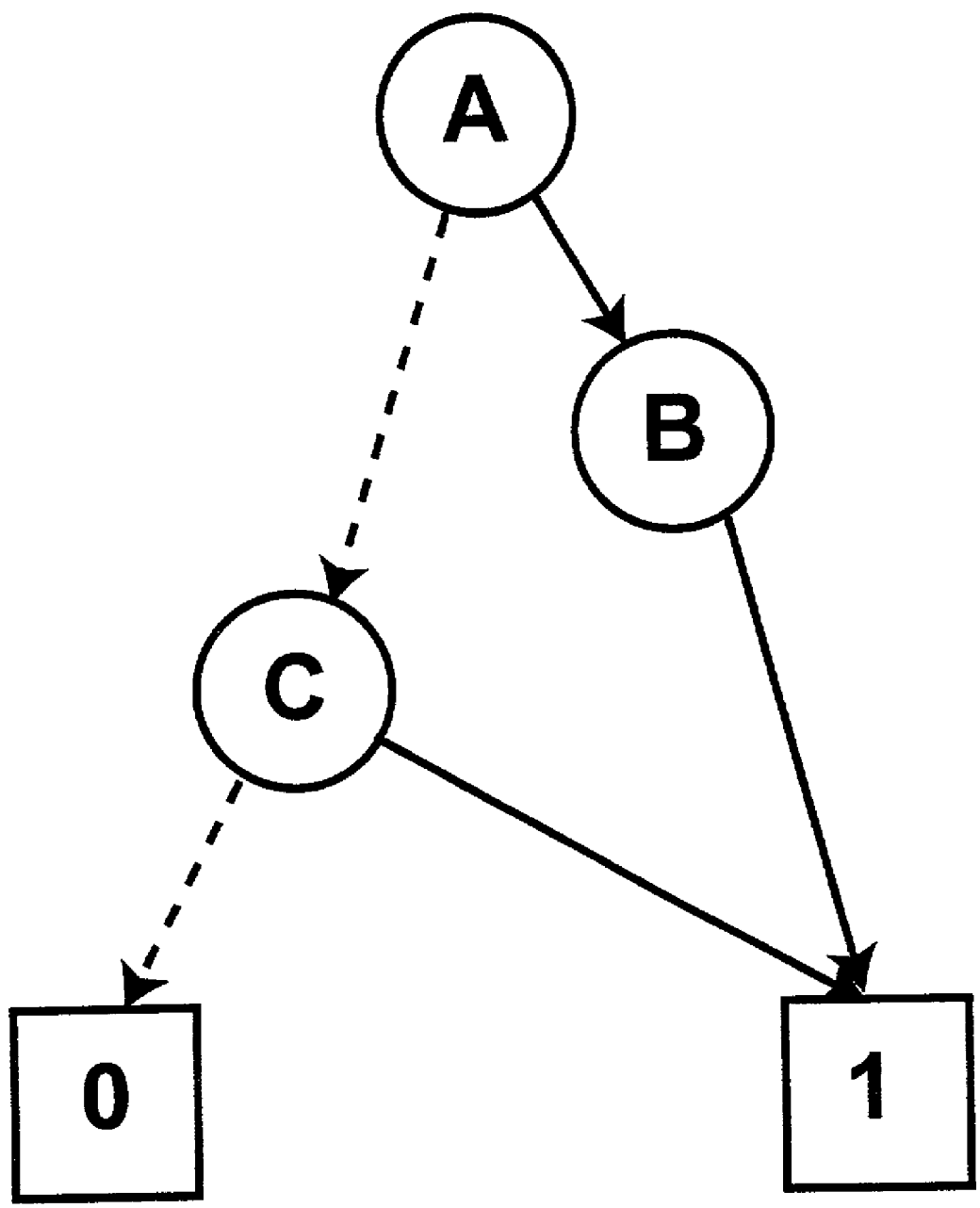
FIG. 4 is a binary decision diagram (BDD) for an exemplary expression.

Each non-terminal node includes two branches (i.e., an out-degree of two) that connect it to lower nodes: a high-edge branch that corresponds to the THEN statement (i.e. when the variable is TRUE), and a low-edge branch that corresponds to the ELSE statement (i.e., when the variable is FALSE). Referring to FIG. 4, the node A has a high-edge (full line) that connects it to the node B and a low-edge (dotted line) that connects it to the node C. A Boolean expression is evaluated by operating an each node until a terminal node that indicates 0 or 1 is reached.

A particularly compact form of a BDD is a reduced, ordered BDD (ROBDD). A BDD is ordered if all paths through the graph result in the same linear order of variables. A BDD is reduced if no two nodes correspond to the same variable and have the same low and high successors and if no single node has the same low and high successor. ROBDDs can be implemented as software, e.g., using a look-up table that indicates at least three items: the variable corresponding to each node, its low successor and its high successor. One implementation is the so-called "Vanilla" ROBDDs of the "BuDDY library" from the Department of Information Technology, Technical University of Denmark, Building 344, DK-2800 Lyngby, Denmark.

Consider the expression:

$$(A \wedge B) \vee C \quad (11)$$

The ROBDD for the expression (11) is diagrammed in FIG. 4. The implicants of expression (11) are listed in Table 2. For example, in the set {A, C}, membership of A is not required for the expression (11) to be TRUE. A can be removed from the set {A, C} to form the set: {C}. Membership of C is essential for the expression (11) to be TRUE. The set {C} is, thus, a prime implicant of the expression (11).

TABLE 2

Implicants of Expression (11)

| Implicant Sets | Note |
|---|---|
| {A, B} | Prime |
| {A, B, C} | |
| {A, C} | |
| {B, C} | |
| {C} | Prime |

The diagram makes evident that there are two paths for evaluating the expression as TRUE (i.e., "1"). The first path is if C is TRUE, independent of A or B. The second path (tracing up the diagram) is if B is TRUE and A is TRUE. These two paths correspond to the two prime implicants of the expression (4).

There are standard techniques for counting/extracting implicants or equivalently the sets of propositions. Each path P in BDD from the root node to the "1" terminal node corresponds to one or more implicants as follows:

If the path P takes the "1" (high) edge from a node labeled "q" then the proposition "q" is in the implicant. If the path takes the "0" (low) edge from a node labeled "q" then the proposition "q" is not in the implicant. If the path does not pass through a node labeled "q" then one can chose whether or not to include "q" in the implicant. This non-determinism is why a single path may correspond to multiple implicants.

Counting the number of implicants can be done efficiently without generating them by a bottom-up labeling algorithm.

To identify solutions for the minimal set inquiries, a ROBDD is constructed for the characteristic function.

Computing the BDD of a Characteristic Function. With respect to the first approach 140, a BDD is computed for $f_Z$, the characteristic function of the specification $Z=<T, R, E'>$. Typically, Z is reduced or maximally reduced by the process 110. The nodes of the BDD correspond to variables that represent the transportable compounds.

Any of the following exemplary methods can be used to construct the BDD for $f_Z$: model theoretic, symbolic transitive closure and symbolic forward rewriting. Symbolic forward rewriting, for example, is suited for coping with intermediate expression swell. For example, the number of BDD variables required by this method is equal to the number of transportable compounds, rather than the total number of compounds.

Symbolic Forward Rewriting is used to construct a BDD for the characteristic function. The BDD is constructed recursively from smaller BDDs. A BDD $\beta_c$ is initialized for each compound c in the reaction system. If the compound is a transportable compound (i.e., $t \in T$), it is represented by a BDD variable $x_t$. For other compounds, the BDD $\beta_c$ is initially set to 0.

Then each reaction in the set R is analyzed. As described in expression (2) above and repeated here, a reaction is represented as:

$$p_1 \wedge \ldots \wedge p_n \rightarrow q_1 \wedge \ldots \wedge q_m \qquad (2)$$

With respect to the LHS, a BDD $\gamma$ is constructed for the reaction LHS such that $\gamma=\beta_{p1} \wedge \ldots \wedge \beta_{pn}$. With respect to the RHS, the BDD for each compound that appears as a product is updated by disjuncting in the BDD $\gamma$ obtained for the LHS. The BDD for $q_i$, $\beta_{qi}$ is replaced with $\beta_{qt} \vee \gamma$. This process is repeated until a fixed point is reached. Then, BDDs are constructed for each of the essential compounds. The BDD for the characteristic function is determined from the component BDDs for each of the essential compounds, i.e., the BDD $f_Z = \wedge_{e \in E} \beta_e$.

In addition to the method described above, a number of heuristics can be applied to facilitate BDD construction.

One heuristic uses strongly connected components formed from a directed graph. Nodes are used to represent reactions. An edge from a node labeled r connects to a node labeled r' iff there exists a compound c that occurs on the RHS of r and the LHS of r'. The graph is partitioned into strongly connected components (SCCs). The SCCs form a poset under reachability. The SCCs of reactions are considered in order. A fixed point BDD analysis is made of each partitioned SCC. This reduces the scale of the computational effort required.

A directed graph can be constructed as follows. A node is provided for each compound. For two compounds C1 and C2 is a directed edge from the C1 node to the C2 node if and only if there is a reaction which uses C1 and produces C2. A compound C2 depends on a compound C1 if and only if there is a directed path from the C1 node to the C2 node. Two compounds C1 and C2 are mutually dependent if and only if there are directed paths from the C1 node to the C2 node and from the C2 node to the C1 node; or equivalently the C1 and C2 nodes are in the same SCC. By partitioning the compounds into SCCs and by considering the SCCs in any linear order that is compatible with the partial order on SCCs induced by reachability, fix-points can be computed with the following guarantee: If a compound C2 depends on a compound C1 then either its BDD is computed in the same fixed-point computation as that for C1 or a later one. In this way, no dependency cycles are introduced and the result of the sequence of fixed point computations will be equal to that of the single (i.e. unpartitioned) fixed-point computation.

Another heuristic avoids superfluous updates of BDDs for individual compounds in the process of recursively constructing the BDD for the characteristic function. There are at least two situations that do not require updating a compound BDD $\beta_c$ with a new value $\beta_c \vee \gamma$. First, if the compound c only appears on the RHS of reactions in an SCC being evaluated, the computation of $\beta_c$ is delayed until the fixed point is reached. Second, the last BDD computed for a LHS of a reaction is stored. If in a subsequent cycle, the BDD is the same, the BDDs for the RHS compounds (i.e., the products) are not updated.

A third heuristic is used to order reactions within each SCC to minimize the number of iterations required to reach the fixed point. Smallest Feedback Vertex Set gives a theoretical bound on the number of iterations but is NP-hard. Optimally, the order of BDD variables is designed to minimize the size of the BDDs produced. One method for ordering compounds within an SCC includes: choose compounds one at a time using the following criteria in strictly decreasing order of importance (i.e., later criteria are only used to break ties on earlier criteria): (1) Maximize the number of already chosen immediate predecessors from within the SCC; (2) Minimize the number of not yet chosen immediate predecessors from within the SCC; and (3) Maximize the number of already chosen immediate predecessors from other SCCs.

If a BDD can be derived for the characteristic function, a compact representation of the problem is attained. It is then straightforward to identify the prime implicants or implicates from the BDD.

Identifying Prime Implicants/Implicates from a BDD for a Characteristic Function. Given a BDD representing a monotone Boolean functions $f: B^k \rightarrow B$, BDDs can be computed for functions which encode the prime implicants and prime implicates of $f$.

The function $f_1: B^k \rightarrow B$ which encodes the prime implicants is as follows:

$$f_1(b_1, \ldots, b_k) = f(b_1, \ldots, b_k) \wedge \bigwedge_{i=1}^{k} \qquad (12)$$
$$(b_i \rightarrow \neg f(b_1, \ldots, b_{i-1}, 0, (b_{i+1}, \ldots, b_k))$$

The function $f_0: B^k \rightarrow B$ which encodes the prime implicates is as follows:

$$f_0(b_1, \ldots, b_k) = \neg f(\neg b_1, \ldots, \neg b_k) \wedge \bigwedge_{i=1}^{k} \qquad (13)$$
$$(b_i \rightarrow f(\neg b_1, \ldots, \neg b_{i-1}, 1, \neg b_{i+1}, \ldots, \neg b_k))$$

A BDD that encodes the set of prime implicants or prime implicates can be efficiently analyzed to determine each member of the set; determine the smallest members of the set; and determine the largest members of the set.

Moreover, the number of members of the set can be efficiently counted, e.g., in a case where extracting each member is not desired. For example, the BDD that encodes the set of primer implicants has the property that any path from the root node to the 1 terminal node passes through exactly one node labeled with each of the propositions (BDD variables). Consequently the prime implicants can be extracted by tracing the paths from the root node to the "1" terminal node in the BDD for the set of prime implicants. As the number of prime implicants is equal to the number of such paths, the number of prime implicants can be counted efficiently without tracing all the paths;

Branch and Bound Algorithm

A second approach to finding a solution to the posed inquiry is to treat $f_Z$ as a "black box" function. This approach identifies prime implicants incrementally. The search process can be halted at any time, yet still provide at least a partial solution.

Identifying a Prime Implicant by Minimization. If an implicant is available, a prime implicant can be identified from it by the following minimization process. Typically, for a model of a metabolic system the all "1's" vector is an implicant, i.e., (1,1,1, . . . 1) and provides a useful starting point.) The vector v for the implicant, by definition, results in $f_Z(v)=1$. The vector v, which is an implicant of $f_z$, is minimized to a vector v' that is a prime implicant (where v'≦v) of $f_z$, by "flipping" the value of each variable in the vector as follows.

The minimization routine can begin by initializing a vector $u=(u_1, \ldots, U_k)$ to equal v, i.e., u=v. Each cycle of the routine, proceeding from i=1 to i=k, a vector u' is defined if $u_i=1$. u' is defined by $u'=(u_1, \ldots, u_{i-1}, 0, u_{i+1}, \ldots, u_k)$. Thus, the $u_i$ position of u' is flipped from 1 to 0. The characteristic function $f_Z$ is evaluated for u'. If $f_Z(u')=1$, then u is replaced with u'. In other words, the vector with the "flipped" variable is accepted, if the characteristic function is still TRUE. The process is iterated until no more positions in u can be flipped. The routine, in a sense, strips the implicant of unnecessary 1's.

The minimization routine provides a straightforward and unambiguous method for identifying a prime implicant from an implicant. The process does require that the characteristic function be evaluated for multiple Boolean vectors. The evaluation of the vectors in the function can be executed by simple forward rewriting, e.g., using a rewriting language such as MAUDE or PVS.

Finding the Next Prime Implicant. One key challenge, given a set of identified prime implicants $\{p_1, \ldots, p_k\}$, is the identification of a vector w for an implicant is such that $f_Z(w)=1$ and such that w minimizes on to a new prime implicant. The inventors have discovered that Theorem 1 instructs this process. Theorem 1 is as follows:

Theorem 1 Given a monotone Boolean function f with prime implicants $v_1, \ldots, v_n$, there exists another prime implicant iff there exists a minimal choice vector u for $v_1, \ldots, v_n$ such that $f(\neg u)=1$.

For a family of Boolean vectors $v_i, \ldots, v_n \in B^k$, a vector $u \in B^k$ is a choice vector for $v_1, \ldots, V_n$ iff for i=1, . . . , k, $u \wedge v_i$ is not the zero vector. A choice vector $u \in B^k$ is a minimal choice vector if no u'<u is a choice vector. In other words, for each prime implicant vector already identified, a choice vector has in common a "1" at at least one index position.

Figure 5:
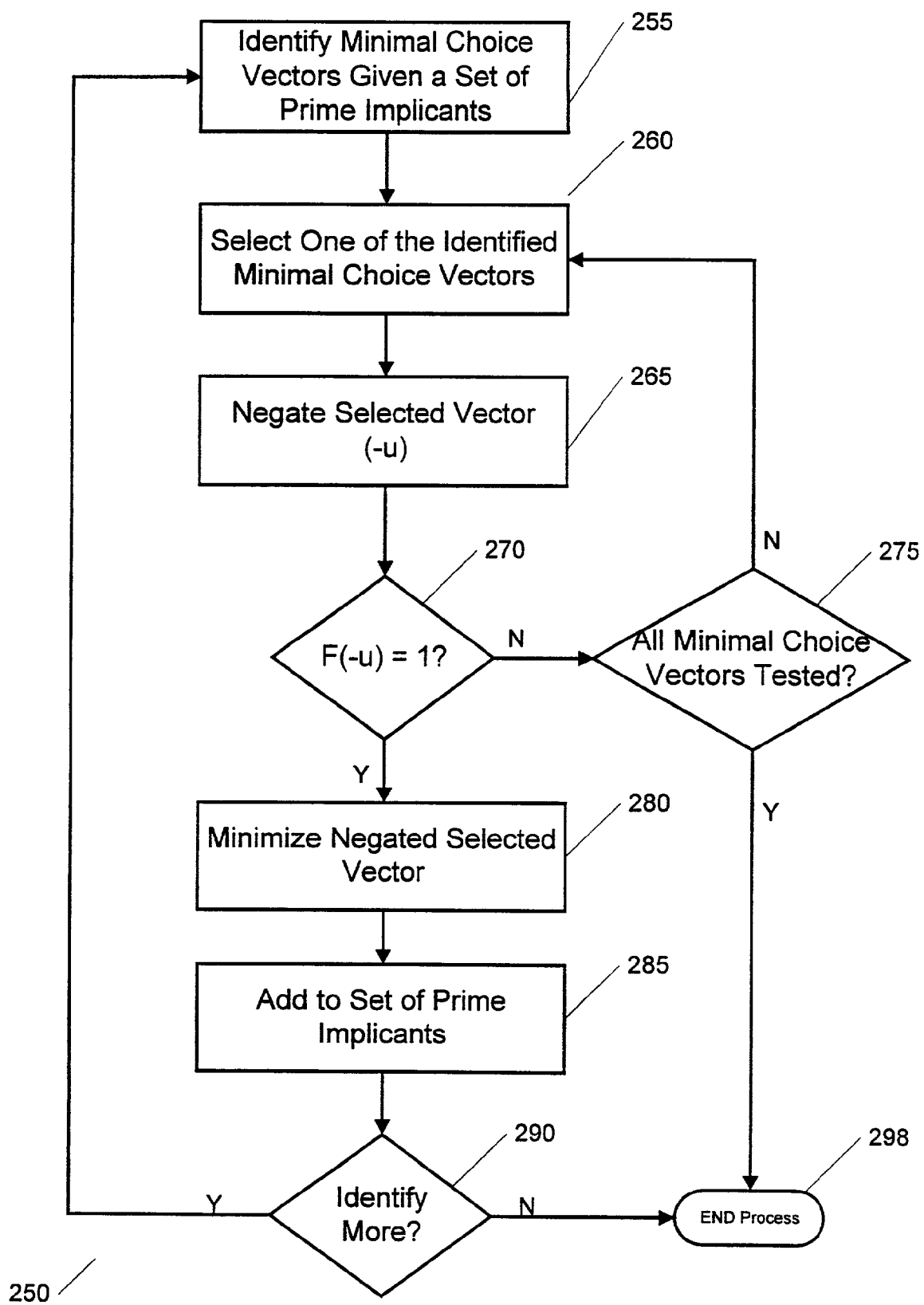
FIG. 5 is a flow chart of an exemplary method for identifying prime implicants.

Referring to FIG. 5, a process 250 for identifying a new prime implicant includes identifying 255 minimal choice vectors for the set of identified prime implicants. For example, the set can include an initial prime implicant that is identified by minimizing the all 1's vector. Iteratively, a minimal choice vector (u) is selected 260 from the set of identified minimal choice vectors. The selected vector is negated 265 (¬u), and then tested 270 in the characteristic function, e.g., by simple forward rewriting. The process is repeated until one of them is found that returns a "1" 270 for the characteristic function (i.e. $f(\neg u)=1$) or until all the minimal choice vectors are tested 275. If the negated vector does return 1 270, then it is minimized 280 as described above. The minimization identifies a new prime implicant which is add to the set of identified prime implicants. At any point in the process, e.g., at 290, a decision can be made whether to continue to identify additional prime implicants or to halt with a partial solution.

Intuitively, the negating insures that the starting vector for the search has a "0" for at least one index position that must be "1" for each previously identified prime implicant. Thus, the starting vector is positioned in a region of vector space that cannot minimize to any previously identified prime implicant.

Enumeration of choice sets can quickly runs into exponential blowup as the number of identified prime implicants increases. This blowup can be made gradual by implementing one or more of the following heuristics.

In one heuristic, a BDD is constructed based on the identified prime implicants. Let $V=(v_1, \ldots v_n) \in B^k$. the function $g_v: B^k \rightarrow B$ is defined by $$g(x_1, \ldots, x_k) = (v_1 \wedge x_1) \vee \ldots \vee (v_k \wedge x_k) \quad (14)$$

For a family of vectors $V_1, \ldots, V_n \in B^k$, the following function is defined: $g^* = g_{V_1} \wedge \ldots \wedge g_{V_n}$. The prime implicants of g* provide the minimal choice vectors for $V_1, \ldots, V_n$. As the prime implicants off are extracted, the BDD representation of g* can be incrementally updated. Any appropriate method can be used to extract the prime implicants of g*.

In another heuristic, the smallest prime implicates/implicants are selected first since their negations produce vectors with the most 1's and are thus, more likely to succeed.

In still another heuristic, a set of failed probes for the prime implicant search is stored in a BDD that could be combined with the one representing g (or its dual) to avoid retesting the same values on future searches.

In yet another heuristic, during the minimization process, forward rewriting is terminated as soon as all the essential compounds are produced. Unassessed positions in the Boolean vector are zero out.

Results

The metabolic pathways of *E. coli* are described in the EcoCyc Database (see, e.g., Karp et al. (2000) *Nucl Acids Res* 28:56-59). These pathways were modeled using some of the implementations described above.

The initial specification included 27 bootstrap compounds, 111 transportable compounds, 1334 reactions, and 39 essential compounds. First, the bootstrap compounds were pruned from the specification. This process required less than 1 second of cpu time.

The specification was further reduced. The number of elements in each aspect of the specification after each reduction step is indicated in Table 3. The upper four rows tabulate results for a specification for which the bootstrap compounds were eliminated. The lower four rows tabulate results for a specification in which the bootstrap compounds were combined with the transportable compounds for comparative purposes.

TABLE 3

*E. coli* Data Set Reduction
[B] = 27, [T] = 111, [R] = 1334, [E] = 39, # compounds = 1061.

|  |  | orig | imp | n&e | l/r | sub | use | cmb |
|---|---|---|---|---|---|---|---|---|
| Bootstrap | [T] | 110 | 110 | 80 | 80 | 80 | 35 | 35 |
| Elimination | [R] | 1279 | 751 | 472 | 313 | 272 | 203 | 174 |
|  | [E] | 38 | 38 | 28 | 28 | 28 | 28 | 28 |
|  | #c | 1013 | 494 | 291 | 291 | 291 | 179 | 179 |
| Bootstrap | [T] | 138 | 138 | 115 | 115 | 115 | 88 | 88 |
| Combination | [R] | 1334 | 801 | 764 | 634 | 560 | 547 | 513 |
|  | [E] | 39 | 39 | 36 | 36 | 36 | 36 | 36 |
|  | #c | 1061 | 542 | 454 | 454 | 454 | 399 | 399 |

Table 3 Legend: "Orig" indicates the number of compounds before the following processes were applied: "imp" (impossible rule deletion 215); "n&c" (needed compound elimination 220 and factoring by equivalence 225); "l/r" (simplify LHS/RHS overlaps 230); "sub" (LHS subsumption 235); "use" (useless compound elimination 240); and "cmb" (reaction combination 245). #c refers to the total number of compounds in the model.

TABLE 4

Prime Implicant Identification

| Specification | Prime Implicants | FP time (secs) | B&B time (secs) |
|---|---|---|---|
| Bootstrap Elimination (BE) | 366 | 4 | 255 |
| BE Reduced | 46 | 3 | 3 |
| BC Reduced | 254793 | 251 | — |

Prime implicants were identified using the fix point (i.e., BDD construction) method, and the branch & bound method. The number of implicants found and the required computation times are summarized in Table 4. With respect to the bootstrap elimination specification, which includes some 174 reactions, both methods, fixed point and branch and bound, identified all 366 prime implicants. For the more complex "Bootstrap Combination Reduced" specification, which includes some 513 reactions, the fixed point method was able to identify a quarter of a million prime implicants in less than 5 minutes.

Exemplary Applications

Solutions and partial solutions to the minimal set inquiries described above (i.e., Inquiries #1, #2, #3, and #4) have a variety of applications, including the following.

Minimal Medium Formulation. A minimal nutrient set identifies a minimal set of compounds that a cell requires for survival. A result from this inquiry can be used to formulate a medium in which the cell of interest is cultured. The cell might be a bacterial cell (e.g., a pathogenic bacterium), a fungal cell, a plant cell, or a mammalian cell. It is also possible to formulate variants of the medium that lack one member of the minimal set, e.g., to verify the determination made from the model.

It is also possible to extend the model to include biochemical reactions that model signaling events in mammalian cells. In this case, the essential compounds include modified forms of signaling proteins that are required for cell proliferation. A solution to the minimal set inquiry may also identify growth factors and hormones that are required for the growth and/or proliferation of a mammalian cell. The model, of course, can also account for variations that depend on the cell type of the mammalian cell.

Further, minimal nutrient sets may be derived for two different cell systems. The sets are compared to identify a minimal set that supports growth of one of the cells, but not the other. Culturing a sample that contains the two different cells in a medium formulated on the basis of such a set results in enrichment of one of the two cells. This approach can be used, for example, to selectively cultivate a particular bacteria from a patient sample that contains many bacteria, design an agricultural scenario that favors growth of a crop relative to opportunistic vegetation, and cultivate particular cell types from a multi-cellular organism.

In another approach, the comparison is not made at the level of minimal sets, but using the characteristic functions. The characteristic function for a cell for which growth is desired is conjoined to the negated function for a cell for which growth is not desired, i.e., $(f_{Zgood} \wedge \neg f_{Zbad})$. The resulting function is then solved to identify compounds that differentially allow growth of the cell for which growth is desired.

Minimal Proof Sets. A minimal proof set (i.e. a solution to Inquiry #2) identifies the minimal reactions that are required for a cell to survive. A solution to this inquiry, for example, provides a formal proof of the model itself. It also can be used to identify reactions that should be deleted in the model in order to bring the model in to correspondence with experimental data.

Further, the set of minimal required reactions also suggests targets for pharmacological inhibition. Inhibiting just one of the targets would prevent the cell from surviving. Minimal sets of reactions can be determined for a cell that is targeted and a cell that is not targeted. The sets are compared to identify a reaction that is in a minimal set of the targeted cell, but is not in a minimal set of the non-target cell. The target and non-target cells might be, respectively, a pathogen and a host cell (e.g., bacterium and intestinal cell; malarial cell and blood cell; fungus and plant cell; and so on) or a cancer cell and a normal cell.

As described above, the comparison can also be made at the level of the characteristic functions.

Least Cost Models

The models can also include various cost factors that are used to identify the more relevant minimal sets that are derived from a model. In this implementation, each proposition for a compound or reaction is associated with a cost $c_p$. The cost is included in the BDD for the characteristic function of the model. The low-edge of a BDD node is labeled with 0 and the high-edge of the node is labeled with $c_p$. The cost for a particular prime implicant is the sum of edge labels obtained on the shortest path from root to the 1 terminal. These least cost implicants can be obtained in linear time.

If all the costs are equal, e.g., $c_p=1$, then the algorithm identifies the smallest prime implicant. Least cost implicates can be found by the dual method.

Costs can be assigned based on real-world practicality. For example, in identifying reactions to target, reactions for which inhibitors are known or easily obtained are assigned a low cost. Reactions that are difficult to target are assigned a high cost. Reactions that are extracellular or that involve proteases might be considered lower cost than reactions involved in gene expression.

In another example, which relates to formulating a minimal medium, compounds which are stable, easily prepared, and absorbable by cells are assigned a low cost whereas compounds that are materially expensive, unstable, and difficult to formulate are assigned a higher cost.

Other Biological Models

The methods and models described here can also encompass propositions that relate to different physical locations. The model is modified such that each proposition is a pair, e.g., <compound, location>. Separate propositions for the same compound can be made for different locations. For example, the model can separately consider the different compartments of a cell, e.g., cytoplasm, mitochondria, and nucleus. Similarly, the model can specify propositions for different cells, e.g., cells of a multicellular organism, particular cells in different differentiation states.

The methods and models can include, instead of or in addition to metabolic reactions, biochemical reactions related to cell regulation, e.g., including cell signaling, gene expression, and protein translation. See, e.g., Kohn (1999) *Mol. Biol. of the Cell* 10:2703-2734 for examples of biochemical reactions relevant for models of cell regulation. In such a model the compounds include modified forms of proteins, e.g., phosphorylated, proteolyzed, glycosylated, methylated, and ubiquitinated forms. The model also includes relationships which describe the biochemical reactions related to cell regulation. An example of such a reaction is:

Substrate+Kinase→Substrate-*P*     (15)

With respect to signaling pathways which frequently include a series of reactions triggered by a product formed from a previous reaction, each modified protein that is a product of one reaction, can feature as a reactant in another reaction. For example, the MAP Kinase pathway can include:

*MKK+MKKK-P→MKK-P*     (16)

*MAPK+MKK-P→MAPK-P*     (17)

The enzymes, in this case kinases activated by phosphorylation, are expressed as reactants since they are required for product formation although they are not themselves modified by the reaction. In other words, the modifying enzyme (e.g., a kinase) enters on the LHS with the substrate and produces the modified substrate on the RHS. This representation can also be used for modeling the function of enzymes in metabolic pathways.

Other examples of biochemical reactions include protein expression as a result of transcriptional or post-transcriptional activation, protein degradation, protein secretion, membrane polarization or depolarization, and so forth.

A model of cell regulation can be used to provide solutions to an inquiry about input compounds that are required for the cell to attain a particular state, i.e., a production state that is defined by the production of certain target compounds. For example, a production state that represents cell proliferation can include the production of the activated form of a cyclin-dependent kinase (such as CDK2). Activated cyclin-dependent kinases can be formed by binding of cyclins and by activating phosphorylations. These reactions are among the relationships expressed by the model.

The input compounds, i.e., precursor compounds, that determine if the cell proliferative state is attained can include extracellular agents, such as hormones and growth factors that trigger signaling events.

The state of the cell can be defined by the presence (or absence) of particular compounds that are indicators of particular cellular behaviors. For example, the set of essential compounds can be defined by proteins in particular modification states and, likewise, genes that are being expressed. Information about the state of a cell can be obtained, e.g., from gene profiling experiments using microarrays, mass spectroscopy, and other proteomics analyses. These analyses provide qualitative and/or quantitative indications of the level of multiple compounds (e.g., mRNAs and proteins) in a cell. These indications can be mapped to a Boolean representation (e.g., using thresholds or limits of detection as a benchmark). These states can be correlated with particular behaviors, e.g., cell division, cell proliferation, shock, cancer, metastasis, apoptosis, senescence, and neuronal signaling. See also, e.g., U.S. Ser. No. 09/855,458, filed 15 May 2001 for examples of methods for extracting state information from experimental observations.

The models described here can also be used to model chemical reactors, particular those that include chemical and/or biochemical reactions that occur outside a living cell. The chemical reactors can be engineered to the production of a compound of interest (e.g., a pharmaceutical or useful material) or destruction of a compound of interest (e.g., pollutants).

Implementation

The methods and models described herein can be implemented, e.g., using a computer system or, in some simple cases, manually.

For example, the invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory; magnetic disks such as, internal hard disks and removable disks; magneto-optical disks; and CD ROM disks. Any of the foregoing can be supplemented by, or incorporated in, ASICs (application-specific integrated circuits).

Other embodiments are within the scope of the following claims.

What is claimed is:

1. A method for evaluating at least one metabolic pathway and culturing cells, the method comprising:
generating a symbolic model that represents a network comprising chemical reactions of the at least one metabolic pathway;

evaluating the symbolic model to identify a first set of precursor substrates and/or chemical reactions that are sufficient to produce a set of target products or a second set of precursor substrates and/or chemical reactions that are insufficient to produce the set of target products, wherein the symbolic model comprises a Boolean function that returns a predetermined value if the set of target compounds is produced; and culturing cells in a medium selected based upon identification of one of the first and second sets to selectively support viability of the cells.

2. The method of claim 1 in which a plurality of sets that are sufficient are identified.

3. The method of claim 1 in which any arbitrary number of, up to and including all sets that are sufficient are identified.

4. The method of claim 1 further comprising, prior to the evaluating, reducing a number of elements in the model.

5. The method of claim 4 wherein said reducing comprises one or more of the following:

Bootstrap elimination, impossible rule deletion, needed compound elimination, factoring by equivalences, simplifying left hand side/right hand side (LHS/RHS) overlaps, LHS subsumption, useless compound elimination, and reaction combination.

6. The method of claim 1 further comprising expressing the Boolean function in if-then-else normal form.

7. The method of claim 6 further comprising mapping each if-then-else expression of the set to a diagram of nodes, wherein each node of the diagram maps to an expression of the set of if-then-else expressions, depends on a Boolean variable associated with the expression and is directionally connected to two lower nodes in accordance with relationships implied by the expression, wherein each of the two lower nodes is either a node that maps to another expression of the set or a terminal node, and wherein the evaluating comprises identifying a path from a node of the diagram that is not a lower node of any other node to one of the terminal nodes of the diagram.

8. The method of claim 7 wherein the path is a least-cost path.

9. The method of claim 1 in which the network comprises at least 100 chemical reactions.

10. A method for evaluating at least one metabolic pathway and culturing cells, the method comprising:

representing a network of chemical reactions of the at least one metabolic pathway as a symbolic model, the model comprising elements that include compounds comprising at least substrates and products, and reactant-product relationships between compounds;

determining a Boolean function from the symbolic model, wherein the Boolean function returns a predetermined value if the network produces a set of target products;

evaluating the Boolean function to identify a first set of precursor substrates and/or reactant-product relationships that is sufficient to produce the set of target products and/or a second set of precursor substrates and/or reactant-product relationships that is insufficient to produce the set of target products; and culturing cells in a medium selected based upon identification of at least one of the first and second sets to selectively support viability of the cells.

11. The method of claim 10 in which the model comprises at least 100 elements.

12. The method of claim 10 further comprising reducing the number of elements of the model.

13. The method of claim 10 in which the evaluating comprises finding one or more implicants and/or implicates of the Boolean function.

14. The method of claim 13 in which the evaluating comprises finding one or more prime implicants and/or prime implicates of the Boolean function.

15. The method of claim 14 in which the evaluating comprises finding any number up to and including all prime implicants and/or prime implicates of the Boolean function.

16. The method of claim 10 in which the evaluating comprises use of a binary decision diagram.

17. The method of claim 10 in which the evaluating comprises use of a branch-and-bound algorithm.

18. The method of claim 10 in which the evaluating comprises use of a fixed point method.

19. The method of claim 10 in which the model is transformed and the evaluating comprises evaluating a Boolean function determined from the model.

20. The method of claim 19 in which the evaluating identifies a set of relationships that is sufficient to produce the set of target products or a set of relationships that is insufficient to produce the set of target products.

21. A method for evaluating at least one metabolic pathway and culturing cells, the method comprising:

inferring a Boolean function from a chemical reaction network of the at least one metabolic pathway that includes relationships between compounds comprising at least substrates and products, the relationships representing chemical reactions between the compounds including precursor substrates and target products, wherein the Boolean function depends on variables, where each variable indicates a presence of at least one of the precursor substrates, and the Boolean function returns a predetermined value for every case in which at least one of the target products is formed from at least one of the precursor substrates;

evaluating the Boolean function to identify a first set of precursor substrates and/or relationships that is sufficient to produce a set of target products and/or a second set of precursor substrates and/or relationships that is insufficient to produce the set of target products; and culturing cells in a medium selected based upon identification of at least one of the first and second sets to selectively support viability of the cells.

22. The method of claim 21 further comprising identifying a prime implicant or prime implicate of the Boolean function.

23. The method of claim 22 further comprising identifying any arbitrary number, up to and including all prime implicants or prime implicates of the Boolean function.

24. The method of claim 21 further comprising transforming the Boolean function into a binary decision diagram.

25. The method of claim 21 in which inferring comprises recursively constructing a symbolic representation of the Boolean function from the relationships.

26. The method of claim 25 in which the symbolic representation comprises nodes, each node corresponding to a variable.

* * * * *

UNITED STATES PATENT AND TRADEMARK OFFICE
CERTIFICATE OF CORRECTION

PATENT NO. : 7,308,363 B2
APPLICATION NO. : 10/055775
DATED : December 11, 2007
INVENTOR(S) : Steven Mark Eker et al.

It is certified that error appears in the above-identified patent and that said Letters Patent is hereby corrected as shown below:

Title Page
Item (54), and in the Specification, Col. 1, Line 1, (Title): Delete "EVALUATION" and insert -- EVALUATING --, therefor.
Item (56), (Other Publications), Line 7: Before "1999." delete ",".
Item (56), (Other Publications), Line 39: Delete "Genomic" and insert -- Genome --, therefor.
Page 2, Col. 1, Item (56), (Other Publications), Line 4: Delete "Ackers,"The" and insert -- Ackers, "The --, therefor.
Page 2, Col. 1 Item (56), (Other Publications), Line 17: Delete "J" and insert -- J. --, therefor.

In the Specification
Col. 7, Line 57: Delete "P₁" and insert -- $p_1$ --, therefor.
Col. 7, Line 67: Delete "^n" and insert -- $^\wedge p_n$ --, therefor.
Col. 8, Line 1: Delete "P₁," and insert -- $p_1$, --, therefor.
Col. 9, Line 34: Delete "FeSO40." and insert -- FeSO4. --, therefor.
Col. 9, Line 52: Delete "if" and insert -- iff --, therefor.
Col. 10, Line 47: Delete ",fz," and insert --, fz, --, therefor.
Col. 12, Line 29: Delete "I₁." and insert -- $l_l$. --, therefor.
Col. 12, Line 35: Delete "(U₁" and insert -- $(U_l$ --, therefor.
Col. 12, Line 36: Delete "(1ᵢΛUᵢ" and insert -- $(l_l{}^\wedge U_l$ --, therefor.
Col. 13, Line 13: Delete " ⌷ " and insert -- | --, therefor.
Col. 14, Line 16: Delete "(≡ᴿ)," and insert -- (≡ᴿ),. --, therefor.
Col. 14, Line 33: Delete "=ᴿT" and insert -- $_{\equiv R} \cap T$ --, therefor.
Col. 15, Line 7: Delete "E'>" and insert -- E> --, therefor.
Col. 15, Line 29: Delete "E'>" and insert -- E> --, therefor.
Col. 17, Line 7: Delete "E'>." and insert -- E>. --, therefor.
Col. 17, Line 55: Delete "C2node" and insert -- C2 node --, therefor.
Col. 17, Line 57: Delete "C2depends" and insert -- C2 depends --, therefor.
Col. 17, Line 58: Delete "C2node." and insert -- C2 node. --, therefor.

Signed and Sealed this
Fifteenth Day of July, 2014

Michelle K. Lee
*Deputy Director of the United States Patent and Trademark Office*

CERTIFICATE OF CORRECTION (continued)
U.S. Pat. No. 7,308,363 B2

Col. 18, Line 45: Delete "$\bigwedge_{i=1}^{k}$" and insert -- $\bigwedge_{l=1}^{k}$ --, therefor.

Col. 18, Line 46: Delete "$b_{i-1}, 0, (b_{i+1},$" and insert -- $b_{l-1}, 0, b_{l+1},$ --, therefor.

Col. 18, Line 54: Delete "$\bigwedge_{i=1}^{k}$" and insert -- $\bigwedge_{l=1}^{k}$ --, therefor.

Col. 18, Line 55: Delete "$b_i \rightarrow f(\neg b_1, \ldots, \neg b_{i-1}, 1, \neg b_{i+1},$" and insert -- $b_l \rightarrow f(\neg b_1, \ldots, \neg b_{l-1}, 1, \neg b_{l+1},$ --, therefor.

Col. 19, Line 3: Delete ""1"" and insert -- "1" --, therefor.

Col. 19, Line 6: After "paths" delete ";" and insert -- . --, therefor.

Col. 19, Line 15: Before "Typically" insert -- ( --.

Col. 19, Line 25: Delete "$U_k$)" and insert -- $u_k$) --, therefor.

Col. 19, Line 27: Delete "$u_{i-1}, 0, u_{i+1},$" and insert -- $u_{l-1}, 0, u_{l+1},$ --, therefor.

Col. 20, Line 23: Before "$V_n$)" insert -- , --.

Col. 20, Line 23: Delete "the" and insert -- The --, therefor.

Col. 20, Line 33: Delete "off" and insert -- of f --, therefor.

Col. 24, Line 56: Delete "CD ROM" and insert -- CD_ROM --, therefor.